United States Patent [19]

Brumm

[11] Patent Number: 5,010,008
[45] Date of Patent: Apr. 23, 1991

[54] STABLE LIQUID ENZYME CONCENTRATE AND PROCESS FOR ITS PRODUCTION

[75] Inventor: Phillip J. Brumm, Lake Zurich, Ill.

[73] Assignee: Enzyme Bio-Systems Ltd., Englewood Cliffs, N.J.

[21] Appl. No.: 282,644

[22] Filed: Dec. 12, 1988

[51] Int. Cl.$^5$ .............................................. C12N 9/28
[52] U.S. Cl. ...................................... 435/202; 435/99; 435/188; 435/832
[58] Field of Search .................. 435/99, 188, 202, 832

[56] References Cited

U.S. PATENT DOCUMENTS

| | | | |
|---|---|---|---|
| 4,284,722 | 8/1981 | Tamuri et al. | 435/94 |
| 4,519,934 | 5/1985 | Eilertsen et al. | 252/174.12 |
| 4,578,352 | 3/1986 | Katkocin et al. | 435/99 |
| 4,613,570 | 9/1986 | Zeman | 435/99 |

OTHER PUBLICATIONS

Pfueller et al., *J. Biol. Chem.*, 244, 48–54 (1969).
Brumm et al., *Food Biotechnology*, 2(1), 67–80 (1988).

*Primary Examiner*—Lester L. Lee
*Assistant Examiner*—E. J. Kraus
*Attorney, Agent, or Firm*—Rockey and Rifkin

[57] ABSTRACT

A process for preparing a stable liquid enzyme concentrate containing the alpha-amylase from *Bacillus stearothermophilus*. A commercial alpha-amylase enzyme preparation is treated with granular starch to absorb the enzyme, and the starch containing the enzyme is separated and then heated in a buffer solution containing calcium ion. The resulting solution, separated from insoluble solid, is then concentrated to give the final product.

12 Claims, No Drawings

STABLE LIQUID ENZYME CONCENTRATE AND PROCESS FOR ITS PRODUCTION

FIELD OF THE INVENTION

This invention relates to a liquid enzyme concentrate containing the alpha-amylase from *Bacillus stearothermophilus* and to a method for its production.

BACKGROUND OF THE INVENTION

In recent years, various heat-stable alpha-amylase enzymes have been developed. Examples of such heat-stable alpha-amylase enzymes include those produced by *Bacillus licheniformis*, U.S. Pat. No. 4,519,934; by *Clostridium thermoamylolyticum*, U.S. Pat. No. 4,578,352; and by *Clostridium thermohydrosulfuricum*, U.S. Pat. No. 4,613,570. Of particular commercial interest are the alpha-amylase enzymes produced by *Bacillus stearothermophilus*. These are described by S. L. Pfueller and W. H. Elliott, *J. Biol. Chem.*, 244, 48 (1969), and in U.S. Pat. Nos. 2,695,863 and 4,284,722.

Liquid *Bacillus stearothermophilus* alpha-amylase preparations are commercially available. Such preparations, however, often contain appreciable amounts of NaCl. The high salt concentration in the enzyme preparation is not desirable when the enzyme is used in liquid detergents and other applications because of its tendency to cause phase separation. The chloride ion is also undesirable as it can cause corrosion of metal containers and equipment. In addition, the commercial liquid alpha-amylase preparations often are dark in color and their concentrates may exhibit a tendency to form a precipitate on storage. For these reasons, the commercially-available *Bacillus stearothermophilus* alpha-amylase liquid preparations have not won ready acceptance by liquid detergent producers and others who need to formulate a cosmetically acceptable enzyme product.

An object of this invention is to provide a liquid enzyme concentrate containing the alpha-amylase of *Bacillus stearothermophilus* which has good enzyme and physical stability, which has little color and is noncorrosive.

The references to *Bacillus stearothermophilus* alpha-amylase cited above describe multistep procedures for preparing purified alpha-amylase enzyme preparations. However, these procedures are suitable only for small-scale preparations and would be far too expensive for the preparation of a commercial product. We have now discovered an inexpensive process which gives a stable liquid enzyme concentrate that is readily adapted to large-scale commercial production.

SUMMARY OF THE INVENTION

In accordance with the present invention, there is provided a process for producing a stable liquid enzyme concentrate containing the alpha-amylase from *Bacillus stearothermophilus* which comprises the steps of:

(a) mixing an aqueous solution of *Bacillus stearothermophilus* alpha-amylase enzyme with granular starch to adsorb the alpha-amylase enzyme;

(b) separating the starch, containing adsorbed alpha-amylase enzyme, from the aqueous solution;

(c) washing the starch containing adsorbed alpha-amylase enzyme;

(d) forming a slurry of the starch containing adsorbed alpha-amylase enzyme in a buffer solution containing calcium ion;

(e) heating the slurry of Step (d) above the gelatinization temperature of the starch to form a solution of the alpha-amylase enzyme and starch hydrolyzate;

(f) separating the solution formed in Step (e) from any insoluble solid; and (g) concentrating the solution obtained in Step (f).

Also provided, in accordance with this invention, is a stable liquid enzyme concentrate containing the alpha-amylase enzyme from *Bacillus stearothermophilus* prepared by the foregoing process having an Absorbance at 450 nanometers (nm) of less than about 4 and a Cl− concentration of less than about 200 millimolar (mM).

DETAILED DESCRIPTION OF THE INVENTION

Any thermostable alpha-amylase enzyme preparation produced by the microorganism *Bacillus stearothermophilus* may be used in the practice of this invention. They are available as concentrated aqueous solutions which contain, in addition to the enzyme, sodium chloride and various other preservatives or stabilizers.

In the practice of this invention, the commercial enzyme solution is diluted with water and the enzyme is then adsorbed from the water solution onto granular starch. Any granular starch may be used for this purpose. A particularly suitable starch is granular corn starch, which is readily available in a comparatively pure form as a product of the corn wet-milling industry.

We have discovered that starch adsorbs much larger quantities of the enzyme from cold solutions. For this reason, it is preferable to carry out the adsorption at temperatures below about 10° C., preferably below about 5° C. but not below a temperature that causes freezing of the solution.

In the practice of this invention, sufficient starch is added so that there is a gram of starch for every 100 to 20,000 units of enzyme, preferably 1 gram of starch for every 1,000 to 10,000 units of enzyme. The enzyme solution is diluted with sufficient water so that starch comprises from about 10% to about 40% by weight, preferably about 20% to about 30% by weight of the resultant mixture of starch, enzyme, and water.

The alpha-amylase enzyme solution is stabilized by the addition of calcium ion. This is conveniently done by adding sufficient calcium acetate to the enzyme solution to give a concentration of about 1 to about 100 mM, preferably about 10 mM. This makes a buffer solution which maintains a pH in the range from about 5.5 to about 7.0, a desired pH range for the adsorption of enzyme onto granular starch.

After the enzyme has been adsorbed on the starch, the starch, containing adsorbed alpha-amylase enzyme, is separated from the aqueous solution. Any standard separation technique, such as centrifugation or filtration, is suitable for the separation.

The starch containing adsorbed enzyme is next washed to remove salts and any colored material. The washing step is preferably carried out at a low temperature (from about 1° C. to about 10° C.), and the wash water contains from about 1 to about 100 mM calcium ion.

After the starch, containing adsorbed enzyme, has been washed, it is slurried in a buffer solution containing calcium ion. The pH of the buffer solution is maintained in the range from about 5.5 to about 7.0, preferably from about 6.0 to about 6.5. The addition of calcium ion and the buffering of the solution are both achieved conveniently by adding sufficient calcium acetate to give from about 1 to about 100 mM, preferably about 10 mM, concentration of this salt.

The slurry of starch, containing adsorbed enzyme, in the buffer solution is then heated above the gelatinization temperature of the starch. This temperature will vary somewhat with the starch used since each variety of starch has a characteristic gelatinization temperature. If the starch used for adsorption is corn starch, it is convenient to heat the slurry at a temperature from about 70° C. to about 80° C. The slurry is held at this temperature until most of the starch dissolves. This is usually accomplished in about 15 to about 30 minutes. Following the heating step, the solution is separated from any insoluble solid and then concentrated to give an enzyme concentrate of the desired concentration.

This separation step is accomplished by conventional separation means, such as centrifugation or filtration. In carrying out the step, it is convenient to add a filter aid, such as diatomaceous earth, to the solution. Concentration of the resultant clarified solution is conveniently carried out by membrane separation processes, such as ultrafiltration.

The clarified, decolorized enzyme concentrate obtained by the process of this invention contains starch hydrolyzate formed when the starch is heated in the presence of the alpha-amylase enzyme. This is another advantage of the process, since the hydrolyzate contributes to the stability of the enzyme.

The enzyme concentrate prepared by the process of this invention has an Absorbance at 450 nm of less than about 4, preferably less than about 2. The $Cl^-$ concentration of the enzyme concentrate is less than about 200 mM, preferably less than about 100 mM.

The alpha-amylase enzyme solutions are analyzed by the following procedure which defines the enzyme unit used in this patent.

alpha-Amylase Assay

Enzyme activity is determined by measuring the decrease in iodine-binding capacity of a soluble starch solution. The solution to be analyzed is diluted with 0.0025 M calcium chloride solution to give a final concentration of about 0.25 unit of activity per ml. One ml of properly diluted enzyme solution is added to 10 ml of a 0.5% soluble starch solution containing 0.03 M acetic acid buffer (pH 6.0) and 0.03 M calcium chloride. The reaction is carried out for 10 minutes at 60° C. One ml of the reaction solution is put in a 100-ml graduated flask containing 50 ml of 0.02 N hydrochloric acid, and after adding 3 ml of 0.05% iodine solution thereto, the total volume is made up to 100 ml by the addition of water. The blue color which develops is measured for Absorbance at 620 nm. The amount of the enzyme required to decompose 10 mg starch in 1 minute at 60° C. is defined as 1 unit.

Enzyme Activity (units/ml) =

$$\frac{D_o - D_s}{D_o} \times \frac{50 (\text{mg Starch})}{10 (\text{min}) \times \frac{10 (\text{mg/min})}{1 \text{ unit}}} \times (\text{dilution factor})$$

where, $D_o$ = Absorbance of control solution (water is added instead of the enzyme solution)

$D_s$ = Absorbance of the reaction solution

Dilution Factor = Volume of diluted enzyme solution (in ml) corresponding to 1 ml of sample The following examples further illustrate the invention. All parts are by weight and all percentages are by weight unless expressly stated to be otherwise.

EXAMPLE 1

A commercial alpha-amylase enzyme from *Bacillus stearothermophilus*, G-ZYME ™, available from Enzyme Bio-Systems Ltd., International Plaza, Englewood Cliffs, N.J., was treated by the following procedure. A solution of 500 grams of the liquid enzyme (3400 units per gram) in 1000 g of 10 mM calcium acetate solution was cooled to 0° C. Then 500 g of granular corn starch (Code 3005, CPC International Inc., International Plaza, Englewood Cliffs, N.J.) was added with stirring. The mixture was held at 4° C. for 30 minutes before the starch, containing the enzyme, was collected by filtration. The solid was washed with 1000 g of 10 mM calcium acetate solution. The wet filter cake, weighing 880 g, was slurried with 620 ml of 10 mM calcium acetate solution. The mixture was then heated to 75° C. and held at this temperature for 15 minutes. The starch was gelatinized and most of the starch was solubilized by this treatment. The solution was next mixed with diatomaceous earth and filtered. The filtrate, 1000 ml, was concentrated by means of a 2-liter Amicon ultrafiltration cell, fitted with a YM10 membrane, to a final volume of 240 ml. The concentrate, which was a pale yellow color, contained $1.44 \times 10^6$ units of alpha-amylase enzyme. This represents an 85% recovery of the enzyme. This concentrate, which contains starch hydrolyzate, exhibits good stability and is compatible with propylene glycol and similar materials used in detergent formulations.

EXAMPLE 2

The general procedure of Example 1 was repeated in a pilot plant using 100 times the quantities of material used in Example 1. This large-scale process gave a concentrate similar to that obtained in Example 1 with good color and stability.

EXAMPLE 3

The procedure of Example 1 was repeated to determine the color and $Cl^-$ concentration of the material before and after the enzyme solution was treated by the process of this invention. Color is measured as the absorbance of a solution at 450 nm. The $Cl^-$ concentration was measured as NaCl using an ion-specific electrode and a Cole-Palmer pH ion meter. The enzyme solution before treatment contained 4200 units/ml and the enzyme solution after treatment contained 5400 units/ml of alpha-amylase activity. The results given in Table I show the reduction in color and $Cl^-$ concentration achieved by the process of this invention.

TABLE I

| Enzyme Solution | Absorbance at 450 nm | $Cl^-$ (mM) |
| --- | --- | --- |
| Before Treatment | 12.3 | 2150 |
| After Treatment | 1.9 | 25.8 |

Thus, it is apparent that there has been provided, in accordance with the invention, a stable, decolorized, liquid enzyme concentrate and a process for its production which fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for producing a stable liquid enzyme concentrate containing the alpha-amylase from *Bacillus stearothermophilus* which consists essentially of the steps of:
   (a) mixing an aqueous solution of *Bacillus stearothermophilus* alpha-amylase enzyme with granular starch to adsorb the alpha-amylase enzyme;
   (b) separating the starch, containing adsorbed alpha-amylase enzyme, from the aqueous solution;
   (c) washing the starch containing adsorbed alpha-amylase enzyme;
   (d) forming a slurry of the starch containing adsorbed alpha-amylase enzyme in a buffer solution containing calcium ion;
   (e) heating the slurry of Step (d) above the gelatinization temperature of the starch to form a solution of the alpha-amylase enzyme and starch hydrolyzate;
   (f) separating the solution formed in Step (e) from any insoluble solid; and
   (g) concentrating the solution obtained in Step (f).

2. The process of claim 1 wherein the granular starch is corn starch.

3. The process of claim 1 wherein calcium acetate is added to the aqueous solution of *Bacillus stearothermophilus* alpha-amylase before it is treated with granular starch to adsorb the alpha-amylase enzyme.

4. The process of claim 1 wherein all of the solutions containing *Bacillus stearothermophilus* alpha-amylase are maintained within the pH range of from about 5.5 to about 7.0.

5. The process of claim 2 wherein Step (e) is carried out at a temperature from about 70° C. to about 80° C. for at least about 15 minutes.

6. A stable liquid enzyme concentrate containing the alpha-amylase enzyme from *Bacillus stearothermophilus* prepared by the steps of:
   (a) mixing an aqueous solution of *Bacillus stearothermophilus* alpha-amylase enzyme with granular starch to adsorb the alpha-amylase enzyme;
   (b) separating the starch, containing adsorbed alpha-amylase enzyme, from the aqueous solution;
   (c) washing the starch containing adsorbed alpha-amylase enzyme;
   (d) forming a slurry of the starch containing adsorbed alpha-amylase enzyme in a buffer solution containing calcium ion;
   (e) heating the slurry of Step (d) above the gelatinization temperature of the starch to form a solution of the alpha-amylase enzyme and starch hydrolyzate;
   (f) separating the solution formed in Step (e) from any insoluble solid; and
   (g) concentrating the solution obtained in Step (f).

7. The stable liquid enzyme concentrate of claim 6 wherein the granular starch is corn starch.

8. The stable liquid enzyme concentrate of claim 6 wherein calcium acetate is added to the aqueous solution of *Bacillus stearothermophilus* alpha-amylase before it is treated with granular starch to adsorb the alpha-amylase enzyme.

9. The stable liquid enzyme concentrate of claim 6 wherein all of the solutions containing *Bacillus stearothermophilus* alpha-amylase are maintained within the pH range of from about 5.5 to about 7.0.

10. The stable liquid enzyme concentrate of claim 7 wherein Step (e) is carried out at a temperature from about 70° C. to about 80° C. for at least about 15 minutes.

11. The stable liquid enzyme concentrate of claim 6 wherein the Absorbance at 450 nm is less than about 4 and the $Cl^-$ concentration is less than about 200 mM.

12. The stable liquid enzyme concentrate of claim 11 wherein the Absorbance at 450 nm is less than about 2 and the $Cl^-$ concentration is less than about 100 mM.